United States Patent [19]

Weithmann et al.

[11] Patent Number: 4,694,024
[45] Date of Patent: Sep. 15, 1987

[54] COMBINATION PRODUCT COMPOSED OF PYRIMIDO-PYRIMIDINES AND O-ACETYLSALICYLIC ACID OR ITS PHARMACOLOGICALLY TOLERATED SALTS, AND ITS USE

[75] Inventors: Klaus U. Weithmann, Hofheim am Taunus; Dirk Seiffge, Münzenberg, both of Fed. Rep. of Germany

[73] Assignee: Hoechst Aktiengesellschaft, Frankfurt, Fed. Rep. of Germany

[21] Appl. No.: 756,674

[22] Filed: Jul. 19, 1985

[30] Foreign Application Priority Data

Jul. 21, 1984 [DE] Fed. Rep. of Germany ........ 3426961
May 3, 1985 [DE] Fed. Rep. of Germany ........ 3515874

[51] Int. Cl.[4] ............................................ A61K 31/62
[52] U.S. Cl. .................................................. 514/161
[58] Field of Search ....................................... 514/161

[56] References Cited

PUBLICATIONS

Bye et al., British Journal of Clinical Pharmacology, 7: 283–286, (1979).
Canadian Cooperative Study Group, New England Journal of Medicine, 299: 53–59, (1978).
Roth and Majerus, Journal of Clinical Investigation, 56: 624–632, (1975).
Basista, et al., Pharmacological Research Communications, 10: 759, (1978).
Masotti et al., The Lancet, iii: 1213–1216, (1979).
Shaikh et al., Prostaglandins and Medicine, 4: 439–447, (1980).
McDonald et al., Prostaglandins, Leukotrines and Medicine, 12: 235–244, (1983).
Platelets and Thrombosis, Mills and Pareti (Eds.), pp. 175–179, Academic Press (1977).
Kadatz et al., Herz-Kreislauf, 12: 519–524, (1973).
Van de Velde, Arch. Int. Pharmacodyn., 256: 327–328.
Brantmark et al., European Journal of Clinical Pharmacology, 22: 309–314, (1982).
Duggan, British Journal of Clinical Pharmacology, 10 (Supp. 2) (1980).
International Meeting on Side Effects of Anti-Inflammatory, Analgesic Drugs (Verona), Sep. 13–15, 1982, (Abstracts).
Goodman and Gilmans The Pharmacological Basis of Therapeutics, (6th Ed.), p. 830.
Wagner, Drug Intelligence Publications, (1st Ed.), pp. 158–165, (1971).
Day et al., Australia and New Zealand Journal of Medicine, 6: 45–50, (1976).
Orozco-Alcala and Baum, Arthritis and Rheumatism, 22: 1034–1037, (1979).
Anslow et al., Current Therapeutic Research, 36: 811–818, (1984).
Leonards, Journal of the American Medical Assoc., 193: 93–98, (1965).
Anslow et al., Pharmacology, 30: 40–44, (1985).
Baum, Journal of Rheumatology, 11: 250–251, (1984).
Bogentoft et al., European Journal of Clinical Pharmacology, 14: 351–355, (1978).
Roberts et al., European Journal of Clinical Pharamcology, 27: 67–74, (1984).
Arfors et al., Nature, 218: 887–888, (1968).
Weichert et al., Haemostasis, 13: 61, (1983).
Seiffge and Dremer, IRCS Medical Science, 12: 91–92, (1984).
Cavalli-Sforza, Biometrie, pp. 49 et seq., (Stuttgart, 1969).
Villa and de Gaetano, Thrombosis Research, 15: 727–732, (1979).
Honour et al., British Journal of Experimental Pathology, 58: 268–272, (1977).
Viinikka and Ylikorkala, British Journal of Pharmacology, 72: 299–303, (1981).
Buchanan et al., Increased Dipyridamole Plasma ... in vivo., Chemical Abstracts, 92: 15588w (1980).
Steele, Trial of Dipyridamole-Aspirin ... Thrombosis, Chemical Abstracts, 94: 132512u, (1981).
Smith, Dipyridamole may be more Effective ... Aspirin, Chemical Abstracts, 95: 108636n, (1981).
Kirchmaier et al., Thrombosis Inhibiting Effect ... Dipyridamole, Chemical Abstracts, 95: 197335d, (1981).
Buchanan et al., Increased Dipyridamole Plasma Concentrations ... In Vivo, Thrombosis Research 15, 813–820.
Chem. Abst., (92), 518800+51916k, (1980).
Chem. Abst., (95), 651z, (1981).

Primary Examiner—Stanley J. Friedman
Attorney, Agent, or Firm—Finnegan, Henderson, Farabow, Garrett & Dunner

[57] ABSTRACT

O-acetylsalicylic acid and a pyrimido-pyrimidine as combination products.

18 Claims, No Drawings

COMBINATION PRODUCT COMPOSED OF PYRIMIDO-PYRIMIDINES AND O-ACETYLSALICYLIC ACID OR ITS PHARMACOLOGICALLY TOLERATED SALTS, AND ITS USE

O-Acetylsalicylic acid is known to be an inhibitor of the aggregation of human blood platelets (for example Br. J. clin. Pharmac. 7 (1979) 283), and it has been reported that it may show valuable therapeutic effects in terms of the prevention of thromboses and strokes (Blood 52 (1978) 1073, N. Engl. J. Med. 299 (1978) 53). The mechanism of action has been reported to be that acetylsalicylic acid inhibits the enzyme cyclooxygenase, which is localized in the blood platelets (J. Clin. Invest. 56 (1975) 624), and thus the biosynthesis of thromboxane $A_2$, which promotes aggregation, is inhibited. However, acetylsalicylic acid is also able to inhibit the cyclooxygenase located in the vessel wall and thus the synthesis of prostacyclin, which inhibits the aggregation. However, since the inhibition of vascular cyclooxygenase is found only at higher doses of acetylsalicylic acid (Pharmacol. Research Commun 10 (1978) 759), consequently the recommendation is that an antithrombotic effect be achieved with low doses of acetylsalicylic acid (Lancet, iii (1979) 1213, Prostaglandins and Medicine 4 (1980) 439). However, there has also been a report that the antithrombotic effect of acetylsalicylic acid increases with increasing doses, and that an optimal effect is achieved under conditions in which there is substantial inhibition of the biosynthesis of both prostacyclin and thromboxane (Prostaglandins, Leukotrienes and Medicine 12 (1983) 235).

Pyrimido-pyrimidines (formula I, see sheet of formulae), by which there are to be understood below, in particular, dipyridamole (2,6-bis-(diethanolamino)-4,8-dipiperidino-(5,4-d)-pyrimidine) and mopidamol (2,6-bis-diethanolamino)-8-piperidino-(5,4-d)-pyrimidine) (see sheet of formulae), are also used clinically as antithrombotic and anti-aggregating medicaments (Platelets and Thrombosis, page 175, Mills and Poreti (Editors), Academic Press, New York (1977)) or for inhibition of metastases. Promotion of the supply of oxygen to ischemic regions in coronary vessels in cases of infarction is evidently also of particular clinical value (Herz-Kreislauf 5 (1973) 519524). Dipyridamole has been described as a stimulator of prostacyclin (Arch. int. Pharmacodyn. 256 (1982) 327). Superadditive actions on induced platelet aggregation have been described for combinations composed of dipyridamole and acetylsalicylic acid (French Patent 2,368,272), and corresponding therapeutic formulations have been proposed. Since no stable uniform mixtures can be obtained from the two components, the French patent mentioned proposes spatial separation of the cdmponents from one another in layered tablets or jacket/core tablets.

A combination product containing 330 mg of acetylsalicylic acid and 75 mg of dipyridamole is already used medically (Asasantin(R), Dr. Karl Thomae GmbH, Biberach). 1 g of acetylsalicylic acid combined with 75 mg of dipyrimadole has also already been used (Europ. J. Clin. Pharmacol. 22 (1982) 309–314). Combination of other pyrimidopyrimidines with acetylsalicylic acid is also known, but these have a ratio of only 0.5 to 0.33 or even less (French Pat. No. 2,390,959).

As shown in Table 1, more potent antithrombotic actions can be achieved with a combination of 5 mg/kg BW of dipyridamole and 22 mg/kg BW (body weight) of acetylsalicylic acid than can be calculated by addition of the actions of the individual substances, i.e. this combination shows not only the superadditive anti-aggregation effects already mentioned above but also a superadditive antithrombotic effect. As described below in more detail, medical use of acetylsalicylic acid can also cause undesirable side effects, for example gastrointestinal irritations. Efforts will therefore have to be made to reduce the acetylsalicylic acid content of the combination, i.e. to choose a ratio of pyrimidopyrimidine to acetylsalicylic acid of greater than 0.5. If the acetylsalicylic acid content for simultaneous administration in the combination mentioned in Table 1 is thus reduced from 22 mg/kg to 5 mg, a significant antithrombotic effect can no longer be detected, i.e. the reduction in the acetylsalicylic acid content which is desirable for reasons of medical tolerance leads to a product without a medical effect.

It has now been found, surprisingly, that administration, successively with a time interval, of (A) pyrimidopyrimidines of the formula I (patent claim 1) or their active metabolites and/or salts of the compounds or metabolites on the one hand, and (B) O-acetyl-salicylic acid or its pharmaceutically tolerated salts on the other hand, in a particular sequence, makes possible an extremely great improvement in the therapy of diseases which are caused or characterized by impaired blood functions or impaired constituents of blood. The sequential administration of component A followed by the administration of acetylsalicylic acid or of its salt, only after 20 to 90 minutes have elapsed, leads to much greater effects than those corresponding to the calculated sum of the actions of the individual components, but also to greater effects than when the two individual substances are administered simultaneously or in reverse sequence. This is all the more surprising since the simultaneous administration of pyrimidopyrimidines, such as dipyridamole, and acetylsalicylic acid leads only to an insignificantly more potent action than is obtained on administration of acetylsalicylic acid alone (see below, Table 1).

Possible pyrimido-pyrimidines are, in particular, dipyridamole (see sheet of formulae, formula Ia) and/or mopidamol (formula Ib), and furthermore, also for example, the compounds Ic and Id and analogs in which one or both —$CH_2$—$CH_2$—OH radicals are replaced by —$CH_2$—$CH_2(CH_3)$—OH or the piperidine radical is replaced by the morpholine radical.

The invention thus relates to combination products containing (A) pyrimido-pyrimidines of the formula I (see patent claim 1), in particular dipyridamole and/or mopidamol, or active metabolites thereof and/or salts of the compounds or metabolites, and (B) O-acetylsalicylic acid or pharmaceutically acceptable salts thereof, the weight ratio of component (A) to component (B) being greater than 0.5, with or without (C) a pharmaceutical excipient, for sequential use in the therapy of diseases caused or characterized by impaired blood functions or constituents of blood, in particular platelets or erythrocytes, in such a manner that component (A) is released (bioavailable) first.

It is surprising that the medical effect obtained according to the invention can be achieved only if the relative acetylsalicylic acid content on administration at successive times (sequential or consecutive administration) is so small that the weight ratio of pyrimidopyrimidine to acetylsalicylic acid does not fall below 0.5. If the ratio of component (A) to the acetylsalicylic acid component (B) is less than 0.5, i.e. if the acetylsalicylic acid content increases, no significant difference can be detected in the antithrombotic action between simultaneous administration and sequential administration according to the invention. It is also surprising that as the acetylsalicylic acid content increases, a better antithrombotic action cannot be achieved than when the pyrimido-pyrimidine components are used according to the invention in combination with substantially smaller amounts of acetylsalicylic acid, namely in a ratio of 0.5 or more, for example 0.8 or 1.

Because of their superadditive effects, the agents according to the invention are thus suitable for antithrombotic, analgesic, anti-aggregation and cystostatic, in particular metastasis-inhibiting, therapy or prophylaxis. The invention therefore also relates to the preparation of the combination product and to its use in human and veterinary medicine. The combination products according to the invention make it possible for the pyrimido-pyrimidine component to be released (be bioavailable) first, i.e. before the acetylsalicylic acid.

It is a surprising advantage that, because of the superadditive effect on sequential administration, the amounts of pyrimido-pyrimidine and acetylsalicylic acid component which are to be administered can be reduced to those amounts which, on administration alone, show only a minimal pharmacological action so that, at the same time, side effects which are elicited by high doses of these medicaments can be diminished. This is of great importance because it is known that acetylsalicylic acid can, in the customary doses, elicit undesired side effects (for example British Journal of Clinical Pharmacology 1980, 10. Suppl. 2 and International Meeting on Side Effects of Antiinflammatory, Analgesic Drugs, Verona, Sept. 13-15, 1982, Abstracts), such as asthma, allergic urticaria, analgesic nephropathy, Reye's syndrome and peptic ulcers. Moreover, the pyrimido-pyrimidines, such as dipyridamole, (see, for example, Goodman and Gilman's The Pharmacological Basis of Therapeutics, 6th edition, New York, 1980) may show undesired side effects. By means of the combination product according to the invention it is now possible, surprisingly, to reduce drastically the dose of acetylsalicylic acid necessary for humans and animals, as well as the amount of dipyridamole or pyrimido-pyrimidines so that there is an even greater improvement in the general toxicological tolerability.

Suitable pharmacologically tolerated salts of acetylsalicylic acid are those with pharmacologically tolerated metal cations, ammonium, amine cations or quaternary ammonium cations. Those of the alkali metals, such as lithium, sodium and potassium, and of the alkaline earth metals, such as magnesium and calcium, are preferred, although it is also possible to use cationic forms of other metals, such as aluminum, zinc and iron.

Pharmacologically tolerated amine cations are, for example, those of primary, secondary or tertiary amines, such as the alkylamines, for example methyl-, dimethyl-, trimethyl-, ethyl-, dibutyl-, triisopropyl-, N-methylhexyl-, benzyl-, β-phenylethylamine, ethylenediamine, diethylenetriamine, piperidine, morpholine, piperazine, mono-, di- and triethanolamine, ethyldiethanolamine, N-butylethanolamine and the like. Other suitable amine salts are the basic amine salts of lysine and arginine. Examples of suitable pharmacologically tolerated quaternary ammonium cations are tetramethylammonium, tetraethylammonium and benzyltrimethylammonium.

Dipyridamole or the pyrimido-pyrimidines can also be in the form of salts, for example as the chloride or fluoride. The pyrimido-pyrimidine component on the one hand, and the acetylsalicylic acid component on the other hand, can also be administered simultaneously to achieve the superadditive effect, but administration in dosage units in a separate form is necessary, even though the components can also be administered in mixtures, in a suitable form, which permit administration sequential in time, for example in a manner such that the acetylsalicylic acid is used in a form in which it can be absorbed only very slowly, for example as the aluminum salt.

The dosage units can be in the form of solid drug forms, such as capsules (including microcapsules which do or do not contain pharmaceutical vehicles), tablets (including coated tablets and pills), or suppositories, where, when capsules are used, the capsule material assumes the function of the vehicle, and the contents can be in the form of, for example, a powder, gel, emulsion, dispersion or solution. Care should be taken that it is ensured that the release of the active compounds is stepwise with respect to time (sequential). It is particularly advantageous and straightforward to prepare oral (peroral) formulations with the two active compounds, which contain the calculated amounts of the active compounds, together with any desired pharmaceutical vehicle. It is also possible to prepare and use an appropriate formulation (suppository) for rectal therapy. Likewise, transdermal and parenteral (intraperitoneal, intravenous, subcutaneous or intramuscular) injection of solutions, for example by means of suitable multichamber injection units, is possible.

The sequential release (bioavailability) of the active compounds is in general achieved by combining the acetylsalicylic acid or pharmaceutically tolerated salts thereof in sustained release form with the desired pyrimidopyrimidine, such as dipyridamole, in the customary manner, for example in tablets, pills or granules.

Thus, for example, jacket/core tablets corresponding to the prior art can be prepared. It has admittedly already been mentioned (claim 7) in French Pat. No. 2,368,272, alongside other possibilities, that the dipyridamole can be contained in the outer layer and the acetylsalicylic acid 5 can be contained in the inner layer of the tablet. The description and claims 6, 8 and 9 also list a number of combination possibilities, according to which the dipyridamole is either contained in the inner layer and surrounded by a layer which is soluble in intestinal juice and the acetylsalicylic acid is surrounded by a layer which is soluble in gastric juice, or according to which both the dipyridamole and the acetylsalicylic acid are surrounded by a layer which is soluble in gastric juice. However, the sequential release, according to the invention, of the active compounds can in no way be achieved with such pharmaceutical formulations.

French Pat. No. 2,368,272 contains no reference to a combination in which the dipyridamole is contained in an outer more soluble layer, in particular a layer which is soluble in gastric juice, and the core is formed by an acetylsalicylic acid tablet which is surrounded by a more insoluble layer, in particular a layer which is insoluble in gastric juice. Precisely with such a combination, however, can the advantageous medicinal effects according to the invention be obtained. The invention also relates to multi-layered tablets in which the layer containing the acetylsalicylic acid guarantees delayed release of the acetylsalicylic acid. It is particularly advantageous, however, if the acetylsalicylic acid is not in the tablet form which is resistant to gastric acid but in the form of microcapsules which are resistant to gastric acid (granules or crystals).

It is in fact known that the use of acetylsalicylic acid tablets which are insoluble in gastric acid presents problems (see Biopharmaceutics and relevant pharmacokinetics. Enteric coatings, Drug Intelligence Publications. 1st edition, 1971, pages 158-165 and Aust. N.Z.J. Med. 6 (1976) 45-50 and Arthritis and Rheumatism 22 (9): 1034-1037, September 1979). Besides increased fecal excretion of blood by the patients thus treated, it should also be mentioned that the bioavailability of the acetylsalicylic acid is widely scattered with respect to time. According to the invention, the release of the pyrimidopyrimidine components and of the acetylsalicylic acid component must be separated by a time interval of 15 minutes to 2 hours, preferably 30 to 90 minutes and in particular 40 to 70 minutes. The absorption of acetylsalicylic acid in the intestine from tablets which are resistant to gastric acid takes place, however, with a wide interindividual range of scatter with respect to time between the treated patients. In many cases, absorption takes place only after 12 hours. (Current Therapeutic Research 36 (1984) 811-818, JAMA 193 (1965) 93-98 and Pharmacology 30 (1985) 40-44). Moreover, such tablets may accumulate in the gastrointestinal tract and thereby cause considerable gastrointestinal side effects (J. of Rheum. 11 (1984) 250-251).

In contrast, small-grained granules which are insoluble in gastric acid are known to have various advantages (see, for example, Current Therapeutic Research 36 (1984) 811-818, European J. Clin. Pharmacol. 14 (1978) 351-355 and Eur. J. Clin. Pharmacol. 27 (1984), 74). The absorption delay from granules is 0.5-1 hour, and at the same time there are substantially smaller interindividual variations between the patients. A time interval of 0.5-1 hour is outstandingly suitable for achieving the therapeutic effects obtainable according to the invention. Another advantage is that the interval of time between the releases, according to the invention, of the active compounds can be very reliably maintained with granules which are resistant to gastric acid. Since precisely the superadditive antithrombotic effects obtainable according to the invention depend on the time interval between the two administrations of active compound or the release, granules which are resistant to gastric acid are particularly suitable for the preparation of the combination products according to the invention. Such acetylsalicylic acid granules can be either in a mixture with the pyrimido-pyrimidine component in an inert pharmaceutical vehicle, such as in a capsule, or in two different compartments of the dose unit. It is also possible, however, to use formulations which contain acetylsalicylic acid in a form which permits slow release in gastric acid e.g. to use a carrier for the acetylsalicylic acid component (B) which contains at least one agent providing a retarding action. For example, acetylsalicylic acid can be bonded to an ion exchanger or suitable metal ions, such as aluminum, or adsorbed on a retarding material or enclosed in a retarding material (for example based on cellulose or polystyrene resin), which is, for example, inside a jacketed tablet, the jacket of which contains the pyrimido-pyrimidine.

The pharmaceutical formulations according to the invention can be prepared by customary processes, such as compression, immersion or fluidized bed processes or by drum coating, and contain vehicles and other customary auxiliaries, such as starch, for example potato, corn or wheat starch, cellulose or its derivatives, in particular microcrystalline cellulose, silica, various sugars, such as lactose, magnesium carbonate and/or calcium phosphates. The coating solution is usually composed of sugar and/or starch syrup, and contains gelatine, gum arabic, polyvinylpyrrolidone, synthetic cellulose esters, surface-active substances, plasticizers and/or pigments and similar additives according to the prior art. All of the customary flow-regulating agents, lubricating agents or lubricants, such as magnesium stearate, and release agents can be used for the preparation of the drug forms.

The ratio by weight of the pyrimido-pyrimidine component to the acetylsalicylic acid can vary within certain limits, as are listed below. The optimum ratio can be determined, for example, using the experimental procedures described below. As a result of the superadditive effect, it is possible for the dosage of the individual components to be reduced decisively by the use according to the invention, and in particular to far below the dosages which would be required to achieve the same effect with individual doses of acetylsalicylic acid or pyrimidopyrimidine or with combined simultaneous administration of acetylsalicylic acid and pyrimidopyrimidine. The known intolerance reactions of pyrimido-pyrimidines and of acetylsalicylic acid are eliminated or at least substantially reduced by the reduction according to the invention of the dosages. In particular, the invention makes it possible to adjust the ratio by weight of dipyridamole to acetylsalicylic acid to more than 0.5. As will be shown below, in fact, the therapeutic effect cannot be increased further by increasing the relative acetylsalicylic acid weight content in the combination according to the invention to values above 2 (corresponding to a ratio of component (A) to (B) of less than 0.5). To achieve the superadditive effect obtainable according to the invention, it is therefore completely unnecessary, and in view of the side effects of the acetylsalicylic acid even harmful, to increase the relative acetylsalicylic acid content two-fold to three-fold or more, as is proposed in French Pat. No. 2,390,959. In contrast, according to the present invention, the ratio by weight of the pyrimido-pyrimidine to the acetylsalicylic acid is greater than 0.5 and up to 30, preferably from 0.6 to 10 and in particular from 0.6 to 3.

It is also possible by use of the experimental prodecures described to determine the optimal time interval between the administration of the pyrimido-pyrimidine component and of the acetylsalicylic acid component, or the optimal rate of release from the pharmaceutical formulations.

Of course, the dose which is to be administered depends on a variety of factors, such as the organism to be treated (i.e. human or animal, age, weight and general state of health), the severity of the symptoms, the disease which is to be treated, (where present) the nature of the concurrent treatment with other medicaments, the frequency of treatment etc. The doses are generally administered up to five times a day, and preferably once to three times a day. The amount of the constituents should lie within the effective dose range which is tolerated by the organism which is to be treated.

For example, the preferred dose of acetylsalicylic acid is, when administered alone to humans, 500 to 2,000, in particular 1,000 mg two or three times a day.

The preferred dose of dipyridamole is, when administered alone to humans, 10 to 150, in particular 25 to 80, mg two or three times a day. It is possible to calculate exactly the relevant amounts from these ratios by weight for the ratio of acetylsalicylic acid to pentoxifylline. Thus, a suitable treatment comprises the administration of, for example, one, two or more, preferably 3 to 8, single doses of the combination products according to the invention, each containing 10 to 150, preferably at least 25 and, in particular, up to 75, mg of dipyridamole, and 10 to less than 300, e.g. to 280, preferably up to 80, mg of acetylsalicylic acid, where the amount is, of course, dependent on the number of single doses as well as the disease which is to be treated, and a single dose can comprise, for example, several tablets which are administered simultaneously. This also applies to the combination according to the invention of mopidamole, of which in general 100-600, preferably 200-250, mg are administered together with 10 to less than 1200, preferaly 100 to 300, mg or 500 mg of acetylsalicylic acid. The amounts in three-component combinations of acetylsalicylic acid and two pyrimido-pyrimidines can also easily be calculated from these data.

The agents according to the invention can be used in the same manner as known antithrombotic agents and agents inhibiting blood platelet aggregation and the metastatic effect. In vivo uses comprise the administration to humans and animals in order to prevent the formation of arterial and venous blood clots, such as to prevent transient ischemic attacks, and for the long-term prophylaxis following myocardial infarctions and strokes, and for arteriosclerosis, as well as for treatment after surgery to prevent postoperative thromboses and for the after-treatment of cancer to prevent or reduce the metastatic effect. Administration to patients who are connected to heart-lung machines and to kidney dialysis is also possible, likewise to patients with artificial heart valves, vessel prostheses etc. Administration for the actual indications for the individual constituents, for example improvement in the supply of oxygen to the cardiac muscle in cases of angina pectoris, as well as alleviation of pain and inhibition of inflammation, is possible.

In vivo investigations

The combination of dipyridamole or mopidamol and acetylsalicylic acid was assessed in vivo using a design of experiment in which an intravascular thrombosis was generated with a laser in the arterioles or venules of the mesentery of a rat. The evaluation was carried out by analysis by vital microscopy (Nature, 218, (1968) 887 and Haemostasis 13 (1983) 61 and IRCS Med. Sci. 12 (1984) 91).

The test substances were administered in 0.9% sodium chloride solution (which contained 1% carboxymethylcellulose (Serva, Heidelberg)) either orally, intraperitoneally or intravenously. Control animals were treated in the corresponding manner but without the test substances. The experimental animals used were male or female Sprague-Dawley or Wistar rats (body weight of about 200 g). The animals which were to be investigated underwent s.c. premedication with 0.1 mg of atropine sulfate in solution and were anesthetized with 100 mg of ketamine hydrochloride and 4 mg of xylazine per kg BW i.p. The investigation made use of arterioles of the mesentery, which was coated with degassed liquid paraffin, having a diameter of about 13 μm. The beam of a 4 W argon laser (supplied by Spectra Physics, Darmstadt) was introduced coaxially, by means of a beam adaptation and adjustment system (supplied by BTG, Munich), into the inverted optical path of a microscope (ICM 405, LD-Epipland 40/0.60; supplied by Zeiss, Oberkochen, Germany). The wavelength used was 514.5 nm, with an energy above the objective of 30.5 mW. The exposure time per single shot was 1/15 sec. All the measuring operations were recorded by video camera (Trinicon tube, Sony, Cologne) and stored in a recorder (Sony, U-matic ¾").

The test substances were administered in various doses to the experimental animals, orally one hour, and on i.v. administration 10 min., before the start of the experiment, control animals receiving the same amount of placebo. The substances were administered as follows: (1) as a single dose, (2) together as a combination or (3) first acetylsalicylic acid and, after 1 h, dipyridamole or mopidamol, and (4) first dipyridamole or mopidamol and, after 1 h, acetylsalicylic acid (Table 1). Table 2 shows the effect of various time intervals.

Evaluation:

The number of shots to induce a defined thrombus is counted. The shot frequency amounts to one lesion at intervals of 2 minutes, and all the thrombi with a minimum size of ¼ of the vessel radius which were formed during the observation period were counted and measured.

The results of the experiment were subjected to statistical analysis using the $\lambda^2$ test (L. Cavalli-Sforza, Biometrie (Biostatistics), Stuttgart, 1969, pages 49 et seq.).

Results

The results are recorded in Table 1. The effects of the single oral doses of 5 mg/kg acetylsalicylic acid or dipyridamole or mopidamol were not significant. Simultaneous administration of 5 mg/kg each of dipyridamole and acetylsalicylic acid also produced no antithrombotic effect in the laser model. This was also the case when acetylsalicylic acid was administered first and dipyridamole was administered after 1 h. In contrast, administration of dipyridamole first and acetylsalicylic acid (in each case 5 mg/kg) after 1 h has a dose-dependent, significant action on the arterioles and venules. The superadditive effect of this sequential administration compared with single doses is clearly evident from the percentage change compared with controls (Table 1) and can be increased further by chronic long-term administration (1 week). In comparison, no further increase in the antithrombotic action was to be achieved by administration of the combination consisting of dipyridamole and a high acetylsalicylic acid content, independently of whether the active compounds were administered simultaneously or in the sequence according to the invention.

The results listed in Table 2 show the optimum time span between the two single doses.

The sequential administration can be carried out using a commercially available perfusion unit with two separately controllable chambers (for example that supplied by Braun, Melsungen, Germany, with motor-driven feed operated separately via a timeswitch). The two chambers of the perfusion unit were filled with dipyridamole solution (corresponding to 5 mg of dipyridamole/kg rat) and with acetylsalicylic acid solution (corresponding to 5 mg/kg) respectively (NaCl solution as above). The timeswitch controlled injection of the acetylsalicylic acid solution took place 20 min.

after the injection of the dipyridamole solution into the caudal vein. In a comparison experiment, both chambers were injected simultaneously. The results corresponded to the measurements obtained after oral administration, i.e. the effects obtained on sequential administration were far greater than those obtained on simultaneous administration.

Pharmaceutical formulations

It is also possible to use suspensions and solid formulations, which are suitable for oral, peroral and rectal administration, to achieve superadditive effects. Examples of formulations of this type for administration to humans contain x mg of dipyridamole and/or mopidamol as the pure substance or as a commercially available finished formulation (Persantin ® coated tablets or ampul solution from Dr. Karl Thomae GmbH, Biberach, Germany) or parts of these finished formulations, combined with y mg of acetylsalicylic acid in the form of commercially available microcapsules (microgranules) (Type M80D from Röhm Pharma GmbH, Weiterstadt, Germany or Encaprin ®, Procter & Gamble, Connecticut, USA). The pharmaceutical vehicles in these combinations are gels, which have been solidified by heating, of (a) 20 percent by weight of gelatine/1 percent by weight of glycerine in water, and (b) 1 percent by weight of agarose in water, and (c) 10 percent by weight ethylcellulose T50 (Hercules GmbH, Hamburg) in acetone/water (80:20% by weight), in each case with 8 percent by weight of dipyridamole or mopidamol, stirred in, or commercially available gelatine capsules (for administration to humans and large animals, preferably size 0 (Kapsugel, Basle)).

The pharmaceutical formulations (see Table 3, Examples 1-6) are added to 10 ml of canine gastric juice or 10 ml of 0.1 N HCl and are maintained at 37° C. in vitro, stirring gently. Aliquots of the supernatant are taken at specified time intervals and are fractionated by high-pressure liquid chromatography and the components determined quantitatively in accordance with the instructions in Journal of Chromatography 231 (1982) 216-221). The pharmaceutical formulations are inserted in duodenal fluid (dog) or sodium bicarbonate solution (pH=7.4) in an analogous manner.

In vivo experiments on rats

For the administration, the constituents of the formulations mentioned in Examples 1-6 are in each case reduced to the amounts of active compound described in Table 1 or capsules of size 4 and 5 are used. Table 1 shows that a superadditive, greater antithrombotic effect was achieved with products X, XI and XIII according to the invention which was far higher than on simultaneous administration of the same amounts of the two components. Even with an improved action, a considerable reduction in the acetylsalicylic acid administered and also in the pyrimidopyrimidine administered and hence a considerably lower stress on the body is thus possible.

TABLE 1

Effect of various sequences of administration of pyrimido-pyrimidine and/or acetylsalicylic acid on laser-induced thrombosis in rats

| Experiment | Substance | Dose mg/kg BW p.o. | Number of animals n | Number of lesions/ animal | Number of shots x̄ | SEM | Changes from control absolute | % | $\chi^2$ test |
|---|---|---|---|---|---|---|---|---|---|
| I | Control (placebo) | — | 12 | 48 | 2.17 | 0.01 | — | — | |
| II | Dipyridamole | 5 | 6 | 24 | 2.35 | 0.14 | 0.18 | 8 | |
| III | Mopidamol | 5 | 6 | 24 | 2.50 | 0.19 | 0.33 | 15 | |
| IV | Acetylsalicylic acid | 5 | 6 | 24 | 1.79 | 0.20 | −0.38 | −18 | |
| V | Acetylsalicylic acid | 10 | 6 | 24 | 2.92 | 0.20 | 0.75 | 35 | $p < 0.01$ |
| VI | Acetylsalicylic acid | 22 | 6 | 24 | 2.99 | 0.17 | 0.82 | 38 | $p < 0.01$ |
| VII | Dipyridamole + acetylsalicylic acid simultaneously | 5 +5 | 6 | 24 | 2.25 | 0.19 | 0.08 | 4 | |
| VIII | Dipyridamole + acetylsalicylic acid simultaneously | 5 +10 | 6 | 24 | 2.82 | 0.21 | 0.65 | 30 | |
| IX | Dipyrimadole + acetylsalicylic acid simultaneously | 5 +22 | 6 | 24 | 3.27 | 0.22 | 1.10 | 51 | $p < 0.01$ |
| X | Dipyridamole; acetylsalicylic acid after 1 hour | 5 +5 | 6 | 24 | 3.27 | 0.20 | 1.10 | 51 | $p < 0.01$ |
| XI | Dipyridamole; acetylsalicylic acid after 1 hour | 5 +9.8 | 6 | 24 | 3.10 | 0.18 | 0.93 | 43 | $p < 0.01$ |
| XII | Dipyridamole; acetylsalicylic acid after 1 hour | 5 +22 | 6 | 24 | 3.26 | 0.16 | 1.09 | 50 | $p < 0.01$ |
| XIII | Mopidamol; acetylsalicylic acid after 1 hour | .5 +5 | 6 | 24 | 2.82 | 0.17 | 0.65 | 30 | $p < 0.01$ |

TABLE 2 of pyrimido-pyrimidine and acetylsalicylic acid on laser-induced thrombosis in rats.
Effect of the time interval between the administration of the substances
Dose in each case 5 mg/kg of dipyridamole p.o. then, after the time indicated, 5 mg/kg of acetylsalicylic acid p.o.

| Substance | Number of animals | Number of lesions | x̄ | SEM | % change from the controls | $\chi^2$ test |
|---|---|---|---|---|---|---|
| Control (placebo) | 12 | 48 | 2.17 | 0.01 | — | |
| 0 min | 6 | 24 | 2.25 | 0.19 | 4 | |
| 10 min | 6 | 24 | 2.27 | 0.22 | 5 | |
| 20 min | 6 | 24 | 2.56 | 0.18 | 18 | |
| 30 min | 6 | 24 | 3.23 | 0.21 | 49 | $p < 0.01$ |
| 60 min | 6 | 24 | 3.27 | 0.20 | 51 | $p < 0.01$ |

TABLE 2-continued of pyrimido-pyrimidine and acetylsalicylic acid
on laser-induced thrombosis in rats.
Effect of the time interval between the administration of
the substances
Dose in each case 5 mg/kg of dipyridamole p.o. then, after
the time indicated, 5 mg/kg of acetylsalicylic acid p.o.

| Substance | Number of animals | Number of lesions | $\bar{x}$ | SEM | % change from the controls | $\chi^2$ test |
|---|---|---|---|---|---|---|
| 90 min | 4 | 16 | 3.05 | 0.22 | 41 | p < 0.01 |
| 120 min | 4 | 16 | 2.30 | 0.25 | 6 | |

TABLE 3

| Example | Pharmaceutical vehicle | Content of acetysalicylic acid | Content of pyrimido-pyrimidine | % acetyl-salicylic acid released after (... min) at pH 1.8 | % pyrimido-pyrimidine |
|---|---|---|---|---|---|
| 1 | Capsule | 103 mg (M80D) | 75 mg Dipyridamole | 0 (5)<br>0 (10)<br>0 (30)$^{(x)}$ | 49 (5)<br>89 (10)<br>100 (30) |
| 2 | Capsule | 97 mg (M80D) | 150 mg Mopidamol | 0 (5)<br>0 (10)<br>0 (30)$^{(x)}$ | 45 (5)<br>87 (10)<br>100 (30) |
| 3 | Gelatine | 80 mg (M80D) | 50 mg Dipyridamole | 0 (5)<br>0 (10)<br>0 (30)$^{(x)}$ | 88 (5)<br>100 (10)<br>100 (30) |
| 4 | as 3 | 45 mg (M80D) | 69 mg Dipyridamole | 0 (5)<br>0 (10)<br>0 (30)$^{(x)}$ | 85 (5)<br>100 (10)<br>100 (30) |
| 5 | Agarose | 138 mg (M80D) | 150 mg Dipyridamole | 0 (5)<br>0 (10)<br>0 (30)$^{(x)}$ | 36 (5)<br>76 (10)<br>100 (30) |
| 6 | Suspension of 4 ml of dipyridamole hydrochloride solution and M80D | 20 mg (M80D) | 20 mg Dipyridamole | 0 (5)<br>0 (10)<br>0 (30)$^{(x)}$ | 100 (5)<br>100 (10)<br>100 (30) |

$^{(x)}$The M80D acetylsalicylic acid crystals which are insoluble in gastric acid are dissolved quantitatively at pH 7.4.

Sheet of formulae $R^4$
|
N      N―$R^3$
||     ||
$R^1$―  N
    N
    |
    $R^2$ Dipyridamole
(Ia)    $R^1 = R^3 = $ —N(CH$_2$—CH$_2$—OH)$_2$ $R^2 = R^4 = $ 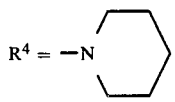

Mopidamol
(Ib)    $R^1 = R^3 = $ —N(CH$_2$—CH$_2$—OH)$_2$
        $R^2 = $ —H $R^4 = $ 

Ic      $R^1$ and $R^2 = $ H
        $R^3 = $ —N(CH$_2$—CH$_2$—OH)$_2$

-continued
Sheet of formulae $R^4 = $ 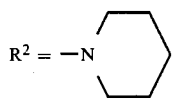

Id      $R^1$ and $R^4 = $ H $R^2 = $ —N⟨hexyl⟩

$R^3 = $ —N(CH$_2$—CH$_2$—OH)$_2$

We claim:
1. A pharmaceutical combination composition containing as essential ingredients
(A) hand a pyrimido-pyrimidine of the formula I

$R^4$
|
N      N―$R^3$
||     ||
$R^1$―  N
    N
    |
    $R^2$ wherein at least one of the groups $R^1$ and $R^3$ represents the group —N(CH$_2$—CHR$^5$OH)$_2$ in which R$^5$ is hydrogen or methyl and at least one of the groups $R^2$ and $R^4$ is the group —N⟨piperidine⟩ or —N⟨morpholine⟩O or an effective metabolite or salt or combination thereof and
(B) hand O-acetylsalicylic acid or a pharmaceutically tolerable salt thereof, the weight ratio between component (A) and component (B) being higher than 0.5 and at most 30, (C) together with or without a pharmaceutical carrier, for the consecutive application in the therapy of diseases which are caused or characterized by impaired blood functions or blood ingredients, such that component (A) is at first released.

2. A composition according to claim 1, wherein component (A) is present in the form of dipyridamol.

3. A composition according to claim 1, wherein the composition is present in the form of a dosage unit to be administered orally or rectally.

4. A composition according to claim 5, wherein the dosage unit contains from 10 to 150 mg dipyridamol and 10 to less than 300 mg acetylsalicyclic acid or an equivalent amount of a salt thereof.

5. A composition according to claim 4, wherein the dosage unit contains from 25 to 75 mg dipyridamol.

6. A composition according to claim 3, wherein the dosage unit contains from 10 to 660 mg of mopidamol and 10 to less than 1200 mg of acetylsalicyclic acid or of an equialent amount of a salt thereof.

7. A composition according to claim 6, wherein the dosage unit contains from 200 to 250 mg of monipdamol.

8. A composition as claimed in claim 6, wherein the dosage unit contains from 100 to 500 mg of acetylsalicylic acid or of an equivalent amount of a salt thereof.

9. A composition according to claim 8, wherein the dosage unit contains from 200 to 250 mg of mopidamol.

10. A composition according to claim 1, wherein the upper limit for the weight ratio between component (A) and component (B) is at 10 and the lower limit is at 0.6.

11. A composition according to claim 10, wherein the upper limit is at 3.

12. A composition according to claim 1, wherein the carrier for the acetylsalicylic acid component (B) contains at least one agent providing a retarding action.

13. A composition according to claim 1, wherein the composition is present in the form of microcapsules, the material of the capsules containing the acetylsalicylic acid component being resistant towards gastric juice or providing a retarded release.

14. A composition according to claim 1, wherein the composition is present in the form of a laminated tablet or multi-layer tablet in which the pyrimidopyrimidine component (A) is contained in the layer first to be resorbed.

15. A method for the treatment of diseases which are caused by impaired blood functions or blood ingredients which comprises administering an effective amount of (A) a pyrimido-pyrimidine of the formula I as defined in claim 1 or an effective metabolite or salt or a combination thereof and (B) O-acetylsalicylic acid or a pharmaceutically tolerable salt thereof in a separate form simultaneously or consecutively in a time difference of 15 minutes to 2 hours such that the pyrimido-pyrimidine component (A) is released to the body prior to the acetylaslicyclic acid component (B) or such that the pyrimidio-pyrimdin component (A) is at first administered and the acetylsalicyclic acid component B is subsequently administered such that the acetylsalicyclic acid component (B) is released 15 minutes to 2 hours later than the pyrimido-pyrimidine component (A), to a human or animal recipient suffering from said diseases.

16. A method for the treatment of a disease which is caused by impaired blood functions or blood ingredients which comprises administering an effective amount of the pharmaceutical composition claimed in claim 1 to a human or animal recipient suffering from said diseaes, thus providing a consecutive release at first of component (A) and subsequently of component (B).

17. The method according to claim 16 for the treatment of a disease which is caused by impaired thrombocytes or erthrocytes.

18. A process for the manufacture of a pharmaceutical composition wherein (A) a pyrimido-pyrimidine of the formula I according to claim 1 or an effective metabolite or salt or a combination thereof and (B) O-acetylsalicylic acid or a pharmaceutically tolerable salt thereof are processed per se or together with (C) a pharmaceutical carrier in a conventional manner to laminated tablets or multi-layer tablets or suppositories with the pyrimido-pyrimdine (A) in the outer layer and the component (B) in the core or the other layer in a form which is less soluble in gastric juice, but soluble in the intestinal juice, or wherein said components are combined in capsules, the weight ratio of component (A) to component (B) being higher than 0.5 and at most 30.

* * * * *

UNITED STATES PATENT AND TRADEMARK OFFICE
CERTIFICATE OF CORRECTION

PATENT NO. : 4,694,024
DATED : September 15, 1987
INVENTOR(S) : Klaus U. WEITHMANN, et al.

It is certified that error appears in the above-identified patent and that said Letters Patent is hereby corrected as shown below:

In Claim 1, Column 12, Line 45; delete the word "hand".

In Claim 1, Column 12, Line 67; delete the word "hand".

In Claim 4, Column 13, Line 13; change "5" to --3--.

In Claim 6, Column 13, Line 20; change "660" to --600--.

In Claim 7, Column 13, Lines 24 & 25; change "monipdamol" to --mopidamol--.

In Claim 15, Column 14, Line 13; change "acetylaslicyclic" to --acetylsalicylic--.

UNITED STATES PATENT AND TRADEMARK OFFICE
CERTIFICATE OF CORRECTION

PATENT NO. : 4,694,024
DATED : September 15, 1987
INVENTOR(S) : Klaus U. WEITHMANN, et al.

It is certified that error appears in the above-identified patent and that said Letters Patent is hereby corrected as shown below:

In Claim 15, Column 14, Line 14; change

"pyrimidio pyrimdin" to --pyrimido-pyrimidine--.

In Claim 15, Column 14, Line 16; change

"acetylsalicyclic" to --acetylsalicylic--.

In Claim 16, Column 14, Line 24; change

"diseaes" to --disease--.

In Claim 18, Column 14, Line 35; change

"acetylsalicyclic" to --acetylsalicylic--.

Signed and Sealed this

Third Day of May, 1988

Attest:

DONALD J. QUIGG

Attesting Officer

Commissioner of Patents and Trademarks